(12) United States Patent
Cahan et al.

(10) Patent No.: US 10,507,267 B2
(45) Date of Patent: Dec. 17, 2019

(54) HIGHLY HYDROPHOBIC ANTIFOULING COATINGS FOR IMPLANTABLE MEDICAL DEVICES

(71) Applicants: International Business Machines Corporation, Armonk, NY (US); Agency for Science, Technology and Research, Singapore (SG)

(72) Inventors: Amos Cahan, Dobbs Ferry, NY (US); Mareva B. Fevre, San Jose, CA (US); James L. Hedrick, Pleasanton, CA (US); Nathaniel H. Park, San Jose, CA (US); Theodore G. van Kessel, Millbrook, NY (US); Rudy J. Wojtecki, San Jose, CA (US); Yi Yan Yang, Singapore (SG)

(73) Assignees: INTERNATIONAL BUSINESS MACHINES CORPORATION, Armonk, NY (US); AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 122 days.

(21) Appl. No.: 15/496,473

(22) Filed: Apr. 25, 2017

(65) Prior Publication Data

US 2018/0303979 A1    Oct. 25, 2018

(51) Int. Cl.
*C09D 183/04* (2006.01)
*A61L 31/10* (2006.01)
(Continued)

(52) U.S. Cl.
CPC ............. *A61L 31/10* (2013.01); *A61L 27/34* (2013.01); *A61L 27/507* (2013.01); *A61L 27/54* (2013.01);
(Continued)

(58) Field of Classification Search
None
See application file for complete search history.

(56) References Cited

U.S. PATENT DOCUMENTS

| | | |
|---|---|---|
| 4,565,740 A | 1/1986 | Golander et al. |
| 5,213,898 A | 5/1993 | Larm et al. |
| (Continued) | | |

FOREIGN PATENT DOCUMENTS

| | | |
|---|---|---|
| CA | 2588832 A1 | 5/2006 |
| EP | 0346058 A1 | 12/1989 |
| (Continued) | | |

OTHER PUBLICATIONS

Dong, et al. "SuFEx-Based Synthesis of Polysulfates," Angewandte Chemie International Edition, 2014, 53 (36), pp. 9466-9470, DOI: 10.1002/anie.201403758.

(Continued)

*Primary Examiner* — Dah-Wei D. Yuan
*Assistant Examiner* — Andrew J Bowman
(74) *Attorney, Agent, or Firm* — Cantor Colburn LLP; Vazken Alexanian (57) ABSTRACT

Antibacterial coatings and methods of making the antibacterial coatings are described herein. In particular, a method for forming an organocatalyzed polythioether coating is provided in which a first solution including a bis-silylated dithiol and a fluoroarene is prepared. A second solution including an organocatalyst is prepared. The first solution and the second solution are mixed to form a mixed solution. The mixed solution is applied to a substrate, and the substrate is cured.

16 Claims, 4 Drawing Sheets

Catalytic Cycle for the Organocatalyzed Polymerization of TMS-Protected Dithiols (II) with Fluoroarenes (IV)

(51) Int. Cl.

| | | |
|---|---|---|
| *A61L 29/08* | (2006.01) | |
| *A61L 29/16* | (2006.01) | |
| *A61L 31/16* | (2006.01) | |
| *A61L 27/34* | (2006.01) | |
| *A61L 27/54* | (2006.01) | |
| *A61L 27/50* | (2006.01) | |
| *C08G 75/20* | (2016.01) | |
| *C09D 181/06* | (2006.01) | |
| *C08G 75/0227* | (2016.01) | |
| *C08G 75/0213* | (2016.01) | |
| *C09D 181/02* | (2006.01) | |
| *B05D 5/00* | (2006.01) | |
| *B05D 1/00* | (2006.01) | |
| *B05D 3/02* | (2006.01) | |

(52) U.S. Cl.
CPC ............ *A61L 29/085* (2013.01); *A61L 29/16* (2013.01); *A61L 31/16* (2013.01); *B05D 5/00* (2013.01); *C08G 75/0213* (2013.01); *C08G 75/0227* (2013.01); *C08G 75/20* (2013.01); *C09D 181/02* (2013.01); *C09D 181/06* (2013.01); *A61L 2300/216* (2013.01); *A61L 2300/404* (2013.01); *A61L 2300/606* (2013.01); *A61L 2420/02* (2013.01); *A61L 2430/14* (2013.01); *A61L 2430/20* (2013.01); *A61L 2430/24* (2013.01); *B05D 1/005* (2013.01); *B05D 3/0254* (2013.01); *B05D 2506/10* (2013.01); *B05D 2518/00* (2013.01)

(56) References Cited

U.S. PATENT DOCUMENTS

| | | | |
|---|---|---|---|
| 8,337,792 | B2 | 12/2012 | Westlund et al. |
| 8,895,354 | B2 | 11/2014 | Kugler et al. |
| 9,018,172 | B2 | 4/2015 | Pentelute et al. |
| 9,109,140 | B2 * | 8/2015 | Dooley ................ C09D 183/04 |
| 9,381,276 | B1 | 7/2016 | Joseph et al. |
| 9,399,044 | B2 | 7/2016 | Cheng et al. |
| 2003/0194504 | A1 | 10/2003 | Bilyk et al. |
| 2011/0086172 | A1 | 4/2011 | Snow |
| 2011/0171279 | A1 | 7/2011 | Chisholm et al. |
| 2012/0058355 | A1 | 3/2012 | Lee et al. |
| 2013/0302873 | A1 | 11/2013 | Singh et al. |
| 2014/0004170 | A1 | 1/2014 | Kronen et al. |
| 2014/0113871 | A1 | 4/2014 | Pentelute et al. |
| 2014/0242866 | A1 | 8/2014 | Locklin |
| 2014/0319044 | A1 | 10/2014 | Giannellis et al. |
| 2014/0342954 | A1 | 11/2014 | Ingber et al. |
| 2014/0369953 | A1 | 12/2014 | Purschwitz et al. |
| 2015/0093425 | A1 | 4/2015 | Moore |
| 2015/0148903 | A1 | 5/2015 | Robeson et al. |
| 2015/0249137 | A1 | 9/2015 | Katsuhara et al. |
| 2015/0328378 | A1 | 11/2015 | Schaer et al. |
| 2015/0369771 | A1 | 12/2015 | Richardson-Burns et al. |
| 2016/0002103 | A1 | 1/2016 | Wang et al. |
| 2016/0165926 | A1 | 6/2016 | Medoff |
| 2016/0200967 | A1 | 7/2016 | Mahoney et al. |
| 2016/0228574 | A1 | 8/2016 | Farokhzad et al. |
| 2016/0237305 | A1 | 8/2016 | Advincula et al. |
| 2018/0282556 | A1 | 10/2018 | Cahan et al. |
| 2019/0048208 | A1 | 2/2019 | Cahan et al. |
| 2019/0048226 | A1 | 2/2019 | Cahan et al. |

FOREIGN PATENT DOCUMENTS

| | | |
|---|---|---|
| EP | 2289971 A1 | 3/2011 |
| EP | 2350116 A1 | 8/2011 |
| WO | 2008106194 A1 | 9/2008 |
| WO | 2010038040 A1 | 4/2010 |
| WO | 2014120095 A1 | 8/2014 |
| WO | 2014152423 A1 | 9/2014 |

OTHER PUBLICATIONS

Garcia, et al. "Meisenheimer Complex Inspired Catalyst- and Solvent-Free Synthesis of Noncyclic Poly(aryl ether sulfone)s," Macromolecules, 2014, 47 (23), pp. 8131-8136, DOI: 10.1021/ma501735q.

Higashihara et al. Recent Progress in High Refractive Index Polymers, Macromolecules 2015, 48, (7), pp. 1915-1929, DOI: 10.1021/ma502569r.

Ishikawa "Superbases for Organic Synthesis: Guanidines, Amidines, Phosphazenes and Related Organocatalysts," Wiley Publication, Mar. 2009, 340 pages.

Matsumura, et al. "Synthesis and Properties of Novel Aromatic Poly(thioether-ketone)s as Sulfur-Containing High-Performance Polymers," Macromolecules, 2001, 34 (9), pp. 2848-2853, DOI: 10.1021/ma001666g.

Nakagawa, et al. "Synthesis of Highly Refractive Poly(phenylene thioether) Derived from 2,4-Dichloro-6-alkylthio-1,3,5-triazines and Aromatic Dithiols," Macromolecules, 2011, 44, 23, pp. 9180-9186, DOI: 10.1021/ma2020003.

Nakagawa, et al. "Synthesis of highly refractive poly(phenylene thioether)s containing a binaphthyl or diphenylfluorene unit," Polymer Chemistry, 2012, 3, pp. 2531-2536, DOI: 10.1039/c2py20325a.

A. J. Domb, I. Yudovin-Farber, J. Golenser, N. Beyth, E I. Weiss, QuaternaryAmmonium Polyethyleneimine: Antibacterial Activity. J. Nanomater. 2010, 2010, DOI 10.1155/2010/826343, 13 pages.

A. J. McBain et al., "Microbial Characterization of Biofilms in Domestic Drains and the Establishment of Stable Biofilm Microcosms", Applied and Environmental Microbiology, 69(1), Jan. 2003, pp. 177-185.

B. A. Lander et al., "Extracytoplasmic Stress Responses Induced by Antimicrobial Cationic Polyethylenimines", Current Microbiology, 65(5), 2012, pp. 488-492.

B. Schachter, "Slimy business—the biotechnology of biofilms", Nature Biotechnology, 21(4), Apr. 2003, pp. 361-365.

Behlau, I., Mukherjee, K., Todani, A. et al. (2011). Biocompatibility and biofilm inhibition of N, N-hexyl, methyl-polyethylenimine bonded to Boston Keratoprosthesis materials. Biomaterials, 32(34), 32 pages.

C. G. Kumar et al., "Significance of microbial biofilms in food industry: a review", International Journal of Food Microbiology, 42(1), 1998, pp. 9-27.

C. Tedjo, "Bacteria-surface interaction in the presence of proteins and surface attached poly(ethylene glycol) methacrylate chains", Journal of Biomedical Materials Research Part A, 82(2), 2007, pp. 479-491.

C. Wiegand et al., "Poly(ethyleneimines) in dermal applications: Biocompatibility and antimicrobial effects", International Journal of Pharmaceutics, 456(1), 2013, pp. 165-174.

D. Davies, "Understanding biofilm resistance to antibacterial agents", Nature Reviews Drug discovery, 2(2), 2003, pp. 114-122.

D. Han et al., "Synthesis of fluorinated monomer and formation of hydrophobic surface therefrom," RSC Adv., 5, 2015, pp. 22847-22855.

De Prijck, K., De Smet, N., Coenye, T. et al. (2010). Prevention of Candida albicans biofilm formation by covalently bound dimethylaminoethylmethacrylate and polyethylenimine. Mycopathologia, 170(4), 213-221.

Faris, A. H., Rahim, A. A., Ibrahim, M. N. M. et al. (2016). Combination of lignin polyol—tannin adhesives and polyethylenimine for the preparation of green water-resistant adhesives. Journal of Applied Polymer Science, 133(20), 6 pages.

George, S. (2015). Nanomaterial Properties: Implications for Safe Medical Applications of Nanotechnology. Nanotechnology in Endodontics, 45-69.

H. Khalil et al., "Synergy between Polyethylenimine and Different Families of Antibiotics against a Resistant Clinical Isolate of *Pseudomonas aeruginosa*", Antimicrobial Agents and Chemotherapy, 52(5), May 2008, pp. 1635-1641.

I. Banerjee et al., "Antifouling Coatings: Recent Developments in the Design of Surfaces That Prevent Fouling by Proteins, Bacteria, and Marine Organisms", Advanced Materials, 23(6), 2011, pp. 690-718.

(56) References Cited

OTHER PUBLICATIONS

J. A. Shapiro, "Thinking about bacterial populations as multicellular organisms", Annual Reviews in Microbiology, 52(1), 1998, pp. 81-104.

J. Hasan et al., "Antibacterial surfaces: the quest for a new generation of biomaterials", Trends in Biotechnology, 31(5), May 2013, pp. 295-304.

J. S. Price et al., "Controlled release of antibiotics from coated orthopedic implants", Journal of Biomedical Materials Research Part A, 30(3), 1996, pp. 281-286.

J. Yatvin et al., "Durable defense: robust and varied attachment of non-leaching poly"-onium" bactericidal coatings to reactive and inert surfaces", Chemical Communications, 50(67), 2014, pp. 9433-9442.

Khan, S., Ui-Islam, M., Ullah, M. W. et al. (2015). Synthesis and characterization of a novel bacterial cellulose—poly (3,4-ethylenedioxythiophene)—poly (styrene sulfonate) composite for use in biomedical applications. Cellulose, 22(4), 2141-2148.

Kondoh, A., Yorimitsu, H., & Oshima, K. (2006). Nucleophilic aromatic substitution reaction of nitroarenes with alkyl-or arylthio groups in dimethyl sulfoxide by means of cesium carbonate. Tetrahedron, 62(10), 2357-2360.

L. Hall-Stoodley et al., "Bacterial biofilms: from the natural environment to infectious diseases", Nature Reviews Microbiology, 2(2), Feb. 2004, pp. 95-108.

List of IBM Patents or Patent Applications Treated as Related; (Appendix P), Date Filed Apr. 15, 2019, 2 pages.

M. Charnley et al., "Designed polymer structures with antifouling—antimicrobial properties", Reactive & Functional Polymers, 71(3), 2011, pp. 329-334.

M. E. Samberg et al., "Silver Nanoparticles in Biomedical Applications", Nanotoxicology: Progress toward Nanomedicine, CRC Press, 2014, pp. 405-421, Book (Provide upon request).

M. M. Azevedo et al., "Polyethyleneimine and polyethyleneimine-based nanoparticles: novel bacterial and yeast biofilm inhibitors", Journal of Medical Microbiology, 63(9), 2014, pp. 1167-1173.

N. Blanchemain et al., "Vascular prostheses with controlled release of antibiotics: Part 1: Surface modification with cyclodextrins of PET prostheses", Biomolecular Engineering, 24(1), 2007, pp. 149-153.

N. Sahiner et al., "The synthesis of desired functional groups on PEI microgel particles for biomedical and environmental applications", Applied Surface Science, 354, 2015, pp. 380-387.

Notification of Transmittal of the International Search Report and the Written Opinion of the International Searching Authority, International Application No. PCT/IB2018/052075, dated Jul. 26, 2018, 12 pgs.

O'Shea, J. P., Solovyeva, V., Guo, X. et al. (2014). Sequence-controlled copolymers of 2, 3, 4, 5-pentafluorostyrene: mechanistic insight and application to organocatalysis. Polymer Chemistry, 5(3), pp. 698-701.

Peraro, L., Siegert, T. R., & Kritzer, J. A. (2016). Chapter Fourteen-Conformational Restriction of Peptides Using Dithiol Bis-Alkylation. Methods in Enzymology, 580, pp. 303-332.

Raad, I., Hachem, R., Zermeno, A. et al. (1996). Silver iontophoretic catheter: A prototype of a long-term antiinfective vascular access device. Journal of Infectious Diseases, 173(2), pp. 495-498.

S. A. Koplin et al., "Evaluation of the Antimicrobial Activity of Cationic Polyethylenimines on Dry Surfaces", Biotechnology Progress, 24(5), 2008, pp. 1160-1165.

S. Eckhardt et al., "Nanobio Silver: Its Interactions with Peptides and Bacteria, and Its Uses in Medicine", Chemical Reviews, 113(7), 2013, pp. 4708-4754.

S. Q. Liu et al., "Antimicrobial and Antifouling Hydrogels Formed In Situ from Polycarbonate and Poly(ethylene glycol) via Michael Addition", Advanced Materials, 24(48), 2012, pp. 6484-6489.

S. Seesukphronrarak et al., "Synthesis of Fluorene-Based High Performance Polymers. I. Poly(arylene thioether)s with Excellent Solubility and High Refractive Index", Journal of Polymer Science Part A: Polymer Chemistry, 45(14), 2007, pp. 3073-3082.

Secinti, K. D., Ayten, M., Kahilogullari, G. et al. (2008). Antibacterial effects of electrically activated vertebral implants. Journal of Clinical Neuroscience, 15(4), pp. 434-439.

Stoodley, P., & Lappin-Scott, H. M. (1997). Influence of electric fields and pH on biofilm structure as related to the bioelectric effect. Antimicrobial agents and chemotherapy, 41(9), 1876-1879.

W. Cheng et al., "Broad-Spectrum Antimicrobial/Antifouling Soft Material Coatings Using Poly(ethylenimine) as a Tailorable Scaffold", Biomacromolecules, 16(7), 2015, pp. 1967-1977.

Y. He et al., "Synthesis and Characterization of Amphiphilic Monodisperse Compounds and Poly(ethylene imine)s: Influence of Their Microstructures on the Antimicrobial Properties", Biomacromolecules, 13(3), 2012, pp. 612-623.

Z. X. Voo et al., "Antimicrobial coatings against biofilm formation: the unexpected balance between antifouling and bactericidal behavior", Polymer Chemistry, 7(3), 2016, pp. 656-668.

List of IBM Patents or Patent Applications Treated As Related; (Appendix P), filed Oct. 14, 2019, 2 pages.

Amos Cahan et al."Highly Hydrophobic Antifouling Coatings for Implantable Medical Devices", U.S. Appl. No. 16/600,798, Oct. 14, 2019.

* cited by examiner

HIGHLY HYDROPHOBIC ANTIFOULING COATINGS FOR IMPLANTABLE MEDICAL DEVICES

BACKGROUND

The present invention relates generally to antibacterial coatings for preventing and treating bacterial and microorganism colonization, biofilm formation, and infection involving medical devices and surfaces. More specifically, the present invention relates to systems and methods for forming highly hydrophobic coatings using the reaction of a silyl protected dithiol with a perfluoroarene in the presence of an organocatalyst.

The accumulation of microorganisms on wetted surfaces, or biofouling, is a ubiquitous problem for materials in a broad range of applications such as medical devices, marine instruments, food processing, and even domestic drains. Generally, bacteria initiate biofouling via the formation of biofilms, which are formed of highly ordered adherent colonies, most frequently within a self-produced matrix of extracellular polymeric substance.

There are a variety of implantable devices, including, for example, prosthetic joints, heart valves, artificial hearts, vascular stents and grafts, cardiac pacemakers, defibrillators, nerve stimulation devices, gastric pacers, vascular catheters and ports (e.g., Port-A-Cath). Infection is a potential problem for all implanted medical devices—the surfaces of these implanted materials and devices represent areas of local immunocompromise in which bacterial colonization and subsequent biofilm formation is difficult to diagnose and treat. Biofilms are the main culprit for persistent infections, owing to their treatment resistance, the potential release of harmful toxins, and the ease with which the microorganisms spread, which can lead to malfunction of implantable devices on which they develop (e.g. catheter occlusion) or septic emboli seeding microorganisms in remote sites.

Extreme measures such as removal of the infected implanted device from the patient's body are often the only viable management option. Although disinfection techniques and prophylactic antibiotic treatment are used to prevent colonization during procedures, this practice is not 100% effective in preventing perioperative bacterial colonization. Moreover, the risk of bacterial colonization on a prosthetic joint is present long after its implantation. For example, with *S. aureus* bacteremia, the risk for colonization on a prosthetic joint approaches 25 percent.

Antibiotic treatments to eliminate colonization and infection associated with implantable substances and devices are limited in their ability to eradicate bacteria and fungi involved in these processes. There are multiple reasons for this, including reduced antibiotic concentration deep inside the biofilm due to limited diffusion, inability of antibiotics in general to eliminate "the last" pathogen cells (usually accomplished by the immune system, which does not function well in the setting of implantable devices), and the ability of microorganisms to persist, i.e., become metabolically inactive and thus functionally relatively resistant to antibiotics. Antibiotic resistance makes treating device-associated infections even more challenging. In fact, antibiotic resistance is frequently encountered with microorganisms that cause device-associated infections (e.g., Enterococci, Staphylococci).

Consequently, considerable efforts were dedicated in recent years to developing antibacterial surfaces. Such surfaces can be classified into two categories: (i) antifouling surfaces that prevent the adhesion of microorganisms and (ii) bactericidal surfaces that trigger bacteria killing. Typical strategies for the design of antibacterial surfaces involve either supramolecular (non-covalent) coating of the surface or modification of the surface (i.e., chemical modification or structuring). Current technologies, however, suffer from poor long-term antibacterial performance and stability, the undesirable development of bacterial resistance, or limited scalability to an industrial setting.

SUMMARY

The current invention is directed to systems and methods for forming highly hydrophobic coatings using the reaction of a silyl protected dithiol with a fluoroarene in the presence of an organocatalyst to prevent and treat bacterial and microorganism colonization, biofilm formation, and infection.

In some embodiments, a bis-silylated dithiol and a fluoroarene are polymerized in the presence of an organocatalyst to form a highly hydrophobic coating having improved antimicrobial/antifouling properties. After curing, the coating provides the advantage of a versatile technology platform for the economical and large-scale application of antimicrobial materials to medical devices. The antimicrobial properties of the final coating can be tuned by selecting different fluoroarenes for the polymerization reaction.

A coating formed in this manner repels bacteria that would otherwise adhere to the surface of an implantable device. The same technology can be used to prevent colonization of medical equipment such as endoscopes, laparoscopes, endoscopes, and surfaces in the healthcare system (e.g. in the patient environment).

According to one or more embodiments of the present invention, a method for forming an organocatalyzed polythioether coating is provided. The method includes providing a first solution of a bis-silylated dithiol and a fluoroarene. The method further includes providing a second solution of an organocatalyst. The first solution and the second solution are mixed to form a mixed solution. The mixed solution is applied to a surface of a substrate and the substrate is cured. The coating provides the technical benefit of a versatile technology platform for the economical and large-scale application of antifouling and bactericidal materials to the surface of implantable and non-implantable medical devices.

According to one or more embodiments of the present invention, a compound for preventing and treating bacterial and microorganism colonization, biofilm formation, and infection is provided. The compound includes an organocatalyzed polythioether polymer having the substructure:

wherein n is greater than 1. The compound, when applied as a coating, provides the technical benefit of a highly hydrophobic coating having improved antifouling characteristics.

According to one or more embodiments of the present invention, a compound for preventing and treating bacterial and microorganism colonization, biofilm formation, and infection is provided. The compound includes an organocatalyzed polythioether polymer having the general substructure:

wherein n is greater than 1, R is a silyated bis-thiol nucleophile, and Ar is an activated fluoroarene. The compound, when applied as a coating, provides the technical benefit of a highly hydrophobic coating having improved antifouling characteristics.

According to one or more embodiments of the present invention, a compound for preventing and treating bacterial and microorganism colonization, biofilm formation, and infection is provided. The compound includes an organocatalyzed polythioether polymer having the substructure:

wherein n is greater than 1. The compound, when applied as a coating, provides the technical benefit of a highly hydrophobic coating having improved antifouling characteristics.

According to one or more embodiments of the present invention, a method for forming an organocatalyzed polythioether coating on an implantable medical device is provided. The method includes providing a first solution of a bis-silylated dithiol and a fluoroarene. The method further includes providing a second solution of an organocatalyst. The first solution and the second solution are mixed to form a mixed solution. The mixed solution is applied to a surface of the implantable medical device and the mixed solution is cured to form the organocatalyzed polythioether coating. In this manner, the technical benefit of a highly hydrophobic coating is provided.

Implantable medical devices to which a coating of the present invention can be applied include, but are not limited to, a prosthetic joint, a vascular line, stent or graft, a venous filter, a tooth implant, a cochlear implant, a metal used for bone fracture internal fixation, a urinary catheter, a ventriculoperitoneal shunt, a cardiac or nerve pacemaker, a heart valve, or a ventricular assist device.

Other advantages and capabilities of the invention will become apparent from the following description taken in conjunction with the accompanying drawings showing the embodiments and aspects of the present invention.

BRIEF DESCRIPTION OF THE DRAWINGS

The subject matter of the present invention is particularly pointed out and distinctly defined in the claims at the conclusion of the specification. The foregoing and other features and advantages are apparent from the following detailed description taken in conjunction with the accompanying drawings in which:

DETAILED DESCRIPTION

Embodiments of the present invention relate to the discovery and subsequent development of highly hydrophobic coatings using the chemical transformation and polymerization of a silyl protected dithiol and a perfluoroarene in the presence of an organocatalyst via nucleophilic aromatic substitution ($S_NAr$). Various embodiments of the present invention are described herein with reference to the related drawings. Alternative embodiments can be devised without departing from the scope of this invention. It is noted that various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements. The term "selective to," such as, for example, "a first element selective to a second element," means that a first element can be etched and the second element can act as an etch stop. The term "conformal" (e.g., a conformal layer) means that the thickness of the layer is substantially the same on all surfaces, or that the thickness variation is less than 15% of the nominal thickness of the layer.

As used herein, the terms "about," "substantially," "approximately," and variations thereof are intended to include the degree of error associated with measurement of the particular quantity based upon the equipment available at the time of filing the application. For example, "about" can include a range of ±8% or 5%, or 2% of a given value.

Turning now to a description of technologies that are more specifically relevant to the present invention, as previously noted herein, the use and development of new implantable devices is growing as a result of continually advancing therapeutics. While the development of these new implantable devices for health monitoring has the potential to revolutionize personalized medicine and disease diagnosis, it is increasingly essential that these devices are biocompatible, particularly with regards the prevention of bacterial infection and to biofilm formation. Conventional antibacterial materials that leverage antifouling or bactericidal surfaces suffer from poor long-term antibacterial performance and stability, the undesirable development of bacterial resistance, or limited scalability to an industrial setting. Moreover, while bacterial cells' lysis on biocide-functionalized surfaces reduces the rate of biofilm formation, a combination of both antifouling and bactericidal properties is desirable to insure the long-term efficacy of the surfaces.

To this end, highly hydrophobic surfaces have the potential to prevent bacterial adhesion and the formation of biofilms. One approach to generate hydrophobic surfaces is to coat the device with an appropriate polymeric material that is itself highly hydrophobic in nature. Such materials would include polymers containing high fluorine content or long alkyl chains, both of which can impart hydrophobic properties to materials. Given the large commercial availability of dithiols and activated fluoroarenes, the preparation of new polythioethers via nucleophilic aromatic substitution ($S_NAr$) has the potential to provide widespread access to novel, highly hydrophobic materials.

Conventional methods for preparing polythioethers have relied upon utilizing $S_NAr$ between dithiols and activated arenes. These methods, however, typically require the use of a stoichiometric amount of base and extended reaction times. While effective, these conditions are less amenable for the preparation of hydrophobic films, particularly with regard to the generation of stoichiometric amounts of salt. In contrast to reactions between dithiols and activated arenes, the polymerization of silylated alcohols and activated fluoroarenes or sulfonyl fluorides produces the volatile silyl fluoride as a byproduct and is more adaptable to the preparation and curing of polymer films. These reactions are relatively slow, however, and the products are not well-suited to scaling.

Thus, to overcome the limitations of traditional polythioether synthesis via traditional $S_NAr$ condensation and to provide new materials and a highly scalable process for producing highly hydrophobic coatings, a new polymerization reaction has been developed that utilizes an organocatalyzed $S_NAr$ condensation between silylated dithiols and activated fluoroarenes to rapidly generate polythioethers. The use of organocatalysts to trigger this $S_NAr$ reaction results in a step-growth polymerization. Step-growth polymerization, as opposed to chain-growth polymerization, refers to polymerization mechanisms in which bi-functional or multifunctional monomers react to successively form dimers, trimers, longer oligomers, and eventually long chain polymers.

Example methods for forming highly hydrophobic coatings using the reaction of a silyl protected dithiol with a perfluoroarene in the presence of an organocatalyst to prevent and treat bacterial colonization, biofilm formation, or infection and the resulting structures therefrom in accordance with embodiments of the present invention are described in detail below by referring to the accompanying drawings in FIGS. 1-4.

Figure 1:
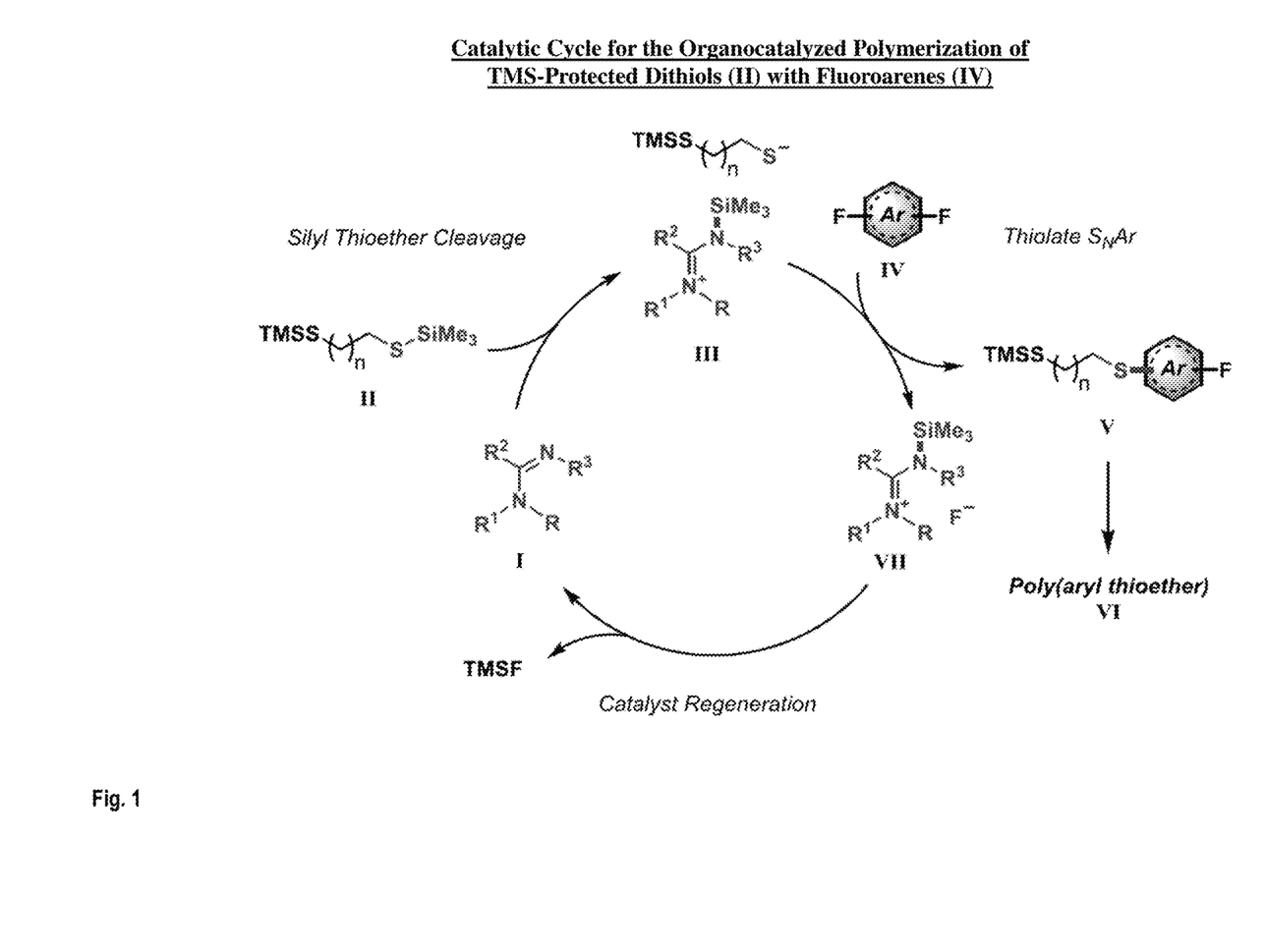
FIG. 1 depicts the catalytic cycle for an organocatalyzed polymerization of a silyl protected dithiol during an intermediate operation of a method of fabricating a highly hydrophobic coating according to one or more embodiments of the present invention.

In some embodiments, the invention relates to the optimal conditions for forming highly hydrophobic coatings (i.e., organocatalyzed polythioethers) using the reaction of a silyl protected dithiol with a perfluoroarene in the presence of an organocatalyst. As previously mentioned herein, traditional polythioether synthesis via $S_NAr$ condensation is relatively slow and subject to scaling difficulties. To overcome these limitations, efforts were focused on developing the conditions for fast polymerization using a catalyst. It was discovered that the reaction of a silyl protected dithiol with a perfluoroarene can exhibit very fast kinetics (e.g., with the reaction being complete in less than two minutes at room temperature) in the presence of an appropriate organocatalyst. FIG. 1 depicts the catalytic cycle for an organocatalyzed polymerization of a silyl (here, TMS) protected dithiol according to one or more embodiments of the present invention.

The fast kinetics exhibited during the organocatalyzed polymerization allow for a polymer coating to be formed at a greatly increased rate relative to polymer films formed using conventional methods for polythioether synthesis. Moreover, the reaction conditions available for the polymerization of a silylated dithiol with a fluoroarene in the presence of an organocatalyst allows for the incorporation of commercially available perfluoroarenes, enabling access to a diverse array of new fluoropolymers. The availability of new fluoropolymers is critical to the development of new, highly hydrophobic films as higher fluorine content confers increased hydrophobicity in the resultant material. In some embodiments, the hydrophobic polymer film coating can be cast or spin-coated on a substrate (see, e.g., FIG. 2).

Figure 2:
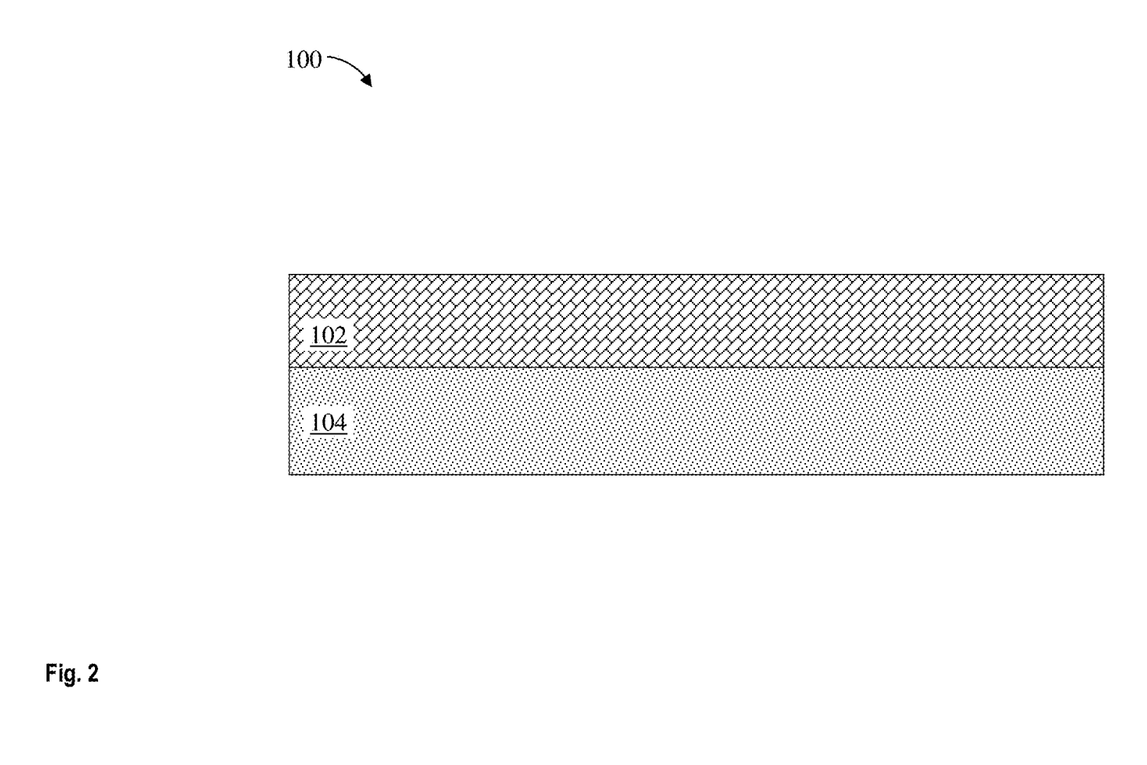
FIG. 2 depicts a cross-sectional view of a structure after forming an organocatalyzed polythioether coating on a surface of a substrate during an intermediate operation of a method of fabricating a highly hydrophobic coating according to one or more embodiments of the present invention.

FIG. 2 illustrates a cross-sectional view of a structure 100 after forming an organocatalyzed polythioether coating 102 on a surface of a substrate 104 during an intermediate operation of a method of fabricating a highly hydrophobic coating according to one or more embodiments. In some embodiments, the coating 102 is formed by polymerizing a silylated dithiol with a fluoroarene, yielding a hydrophobic polymer coating after curing. In some embodiments, the silylated dithiol is a bis-trimethylsilyl protected dithiol which is mixed with hexafluorobenzene and an organocatalyst. In some embodiments, the bis-trimethylsilyl protected dithiol is 2,2,11,11-tetramethyl-3,10-dithia-2,11-disiladodecane (referred to herein as 1a) and the mixture rapidly polymerizes to afford an aryl polythioether (hereinafter, polymer 1b) according to the reaction scheme depicted in FIG. 3. In some embodiments, the bis-trimethylsilyl protected dithiol is the thioether of 4,4'-thiodibenzenethiol (hereinafter, polymer 2a) and the mixture rapidly polymerizes to afford polymers 2b, 2c, 2d, or 2e according to the reaction schemes depicted in FIG. 4.

In some embodiments, the bis-trimethylsilyl protected dithiol is polymerized with hexafluorobenzene in the presence of 1,8-Diazabicyclo[5.4.0]undec-7-ene (more commonly, "DBU"). In some embodiments, the bis-trimethylsilyl protected dithiol is polymerized with the hexafluorobenzene in the presence of 1,5,7-Triazabicyclo[4.4.0]dec-5-ene (triazabicyclodecene, or more commonly, "TBD"). In still other embodiments, the bis-trimethylsilyl protected dithiol is polymerized in the presence of other catalysts, such as, for example, $Et_3N$.

In some embodiments, the coating 102 can be a cast film formed on the surface of the substrate 104. In some embodiments, the substrate 104 is a glass slide. In some embodiments, a first container (e.g., an 8 ml vial) is charged with 1a (e.g., 229 µL, 0.712 mmol), hexafluorobenzene (e.g., 80 µL, 0.712 mmol), and N-methyl-2-pyrrolidone (NMP) (e.g., 1.5 mL). A second container is charged with DBU (e.g., 11 µL, 0.0712 mmol) and NMP (e.g., 0.5 mL). In some embodiments, the DBU solution contained in the second container is added to the contents of the first container and briefly mixed (affording, after mixing, the polymer 1b) before being administered to the surface of the substrate 104 via pipette. Once the substrate 104 is fully coated, the substrate 104 was placed on a hot plate and cured. In some embodiments, the substrate 104 is cured at a temperature of 220 degrees Celsius for six (6) hours. A cured coating 102 formed in this manner provides a contact angle with water of 99 degrees.

In some embodiments, the substrate 104 is a silicon wafer and the coating 102 is spin-coated onto a surface of the wafer. In some embodiments, a solution of polymer 1b is pre-prepared according to one or more embodiments of the present invention. The solution of polymer 1b can then be dissolved in tetrahydrofuran (THF, also known as oxolane) (e.g., 100 mg/mL). In some embodiments, the dissolved solution is placed on the substrate 102 and spin-coated using known spin-coating techniques (affording, after spin-coating, the coating 102). In some embodiments, the coating 102 is spin-coated at 4000 rpm for 30 seconds. A coating 102 formed in this manner provides a contact angle with water of 88 degrees.

Figure 3:
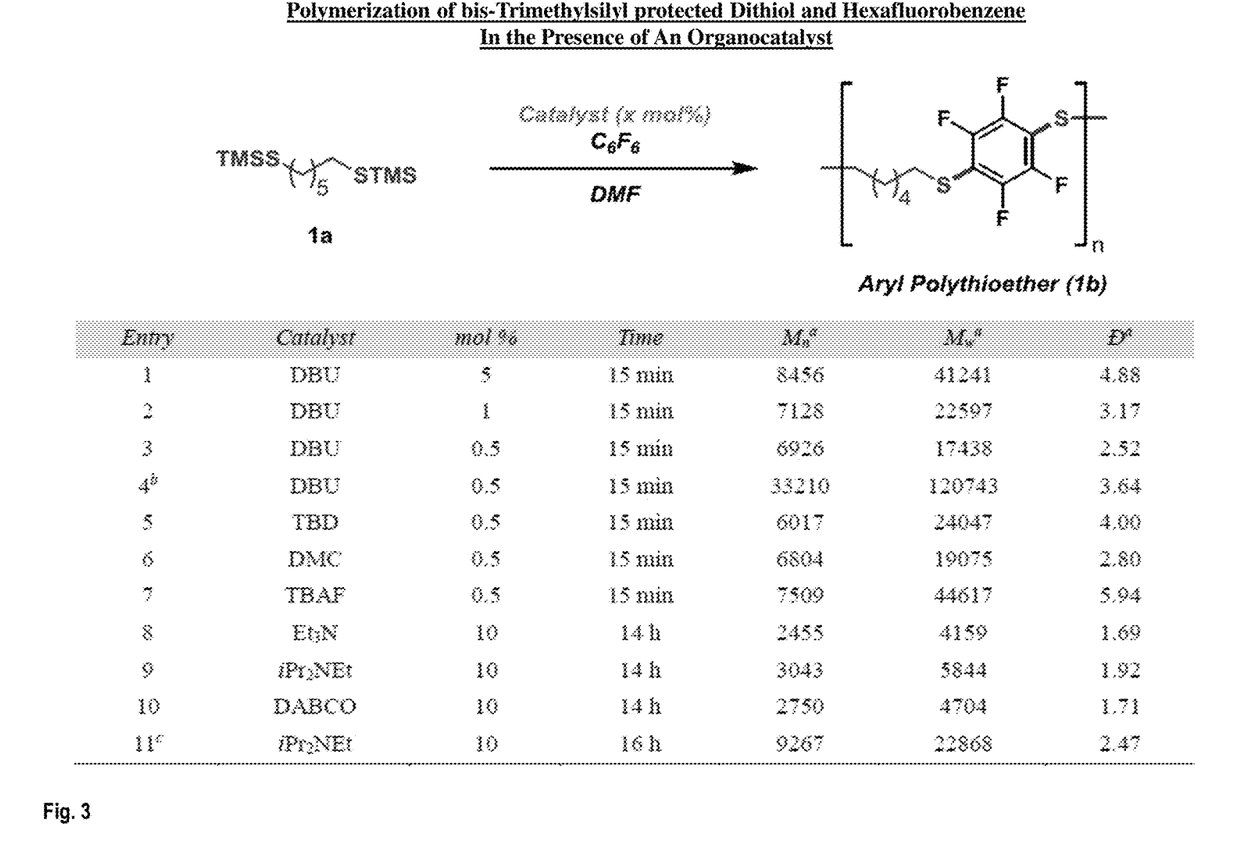
FIG. 3 depicts the polymerization of a bis-trimethylsilyl protected dithiol and hexafluorobenzene in the presence of various organocatalysts according to one or more embodiments of the present invention.

FIG. 3 illustrates the polymerization of 1a and hexafluorobenzene in the presence of various organocatalysts to form the polymer 1b according to one or more embodiments. By reacting 0.25 to 0.5 mmol 1a with 0.25 to 0.5 mmol hexafluorobenzene at room temperature using 5 mol percent DBU as the organocatalyst, a swift exotherm was observed coupled with the formation of fluorotrimethylsilane (TMSF) and a rapid precipitation of polymeric material having a Mn of 8456 g/mol and a dispersity of 4.88 (Entry 1). By lowering the catalyst loading to 1 or 0.5 mol percent, the corresponding Mn and dispersity of the polymers decreased while still affording short reaction times (Entries 2 and 3). Performing the reaction inside a glovebox under strictly anhydrous conditions afforded a higher Mn and dispersity, indicating that the polymerization reaction is sensitive to water and ambient moisture (Entry 4). In some embodiments, the reaction was performed at 100 degrees Celsius (Entry 11). As depicted in FIG. 3, the polymerization of 1a was possible using a variety of catalysts, such as, for example, N,N'-dicyclohexyl-4-morpholineformamidine (DMC), tetra-n-butylammonium fluoride (TBAF), and 1,4-diazabicyclo[2.2.2]octane (DABCO).

Figure 4:
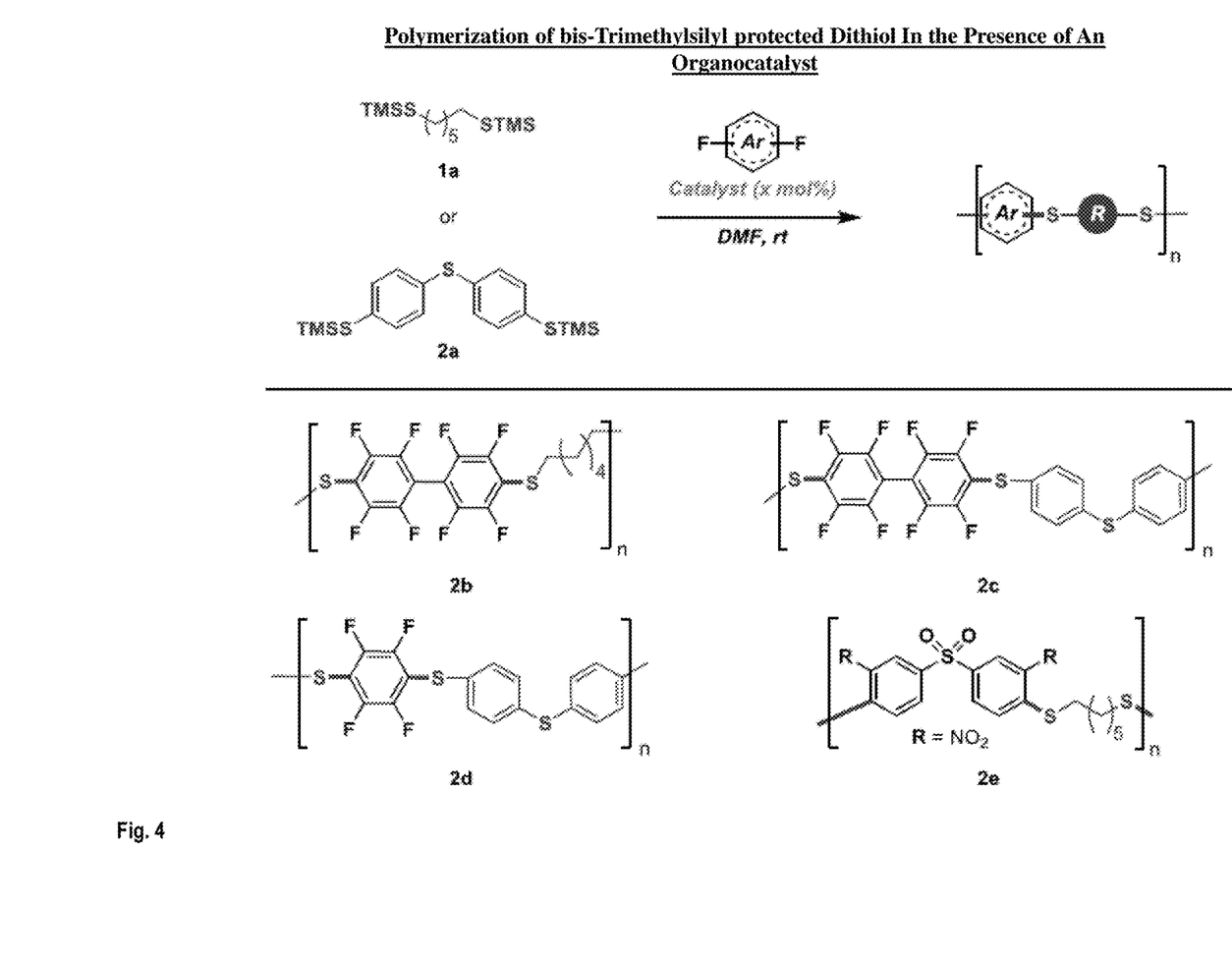
FIG. 4 depicts the polymerization of a bis-trimethylsilyl protected dithiol and a fluoroarene electrophile in the presence of an organocatalyst according to one or more embodiments of the present invention.

FIG. 4 illustrates the polymerization of 1a or 2a and a fluoroarene electrophile in the presence of an organocatalyst to form the polymers 2b, 2c, 2d, and 2e according to one or more embodiments. The reactions depicted in FIG. 4 are carried out using 1a or 2a at a concentration of 0.25 to 0.5 mmol, a fluoroarene electrophile (decafluorobiphenyl, hexafluorobenzene, or bis(4-fluoro-3-nitrophenyl) sulfone) at a concentration of 0.25 to 0.5 mmol, a catalyst at a concentration of 0.25 to 1 mol percent, and 1 molar DMF at room temperature for 5 to 15 minutes according to the following Table:

TABLE 1

| Evaluation of Electrophiles and Nucleophiles for the Synthesis of Poly(aryl thioethers | | | | | | | |
|---|---|---|---|---|---|---|---|
| Entry | Poly. | Cat. | mol % | Mn | Mw | Đ | $T_g$ (° C.) |
| 1 | 2b | DBU | 1 | 15701 | 40353 | 2.57 | 16.7 |
| 2 | 2b | TBD | 1 | 9585 | 27898 | 2.91 | nd |
| 3 | 2c | None | — | 7768 | 47026 | 6.05 | 150.0 |
| 4 | 2d | DBU | 0.25 | — | — | — | 48.0 |
| 5 | 2e | DBU | 0.5 | — | — | — | 28.0 |

Decafluorobiphenyl proved to be an excellent substrate for this reaction and readily polymerized into polymer 2b when 1a was used as the nucleophile using either DBU or TBD as the catalyst (Entries 1 and 2). Advantageously, when decafluorobiphenyl was utilized as a co-monomer with 2a inside a glovebox, no catalyst was necessary to initiate polymerization. Instead, dissolution of both monomers in DMF was sufficient to induce rapid polymerization (i.e., a reaction time of about 5 minutes) to afford the polymer 2c (Entry 3). The polymerization of 2a and hexafluorobenzene in the presence of DBU afforded the polymer 2d (Entry 4).

Non-perfluorinated, yet highly activated aryl electrophiles such as bis(4-fluoro-3-nitrophenyl) sulfone could also be rapidly polymerized under these reaction conditions to form polymer 2e (Entry 5).

As discussed previously herein, the reaction conditions available for the polymerization of a silylated dithiol with a fluoroarene in the presence of an organocatalyst allow for the incorporation of a wide range of commercially available perfluoroarenes. Functionalizing the coating 102 according to one or more embodiments of the present invention with each of these perfluoroarenes can provide a diverse array of new fluoropolymer coatings. Moreover, the presence of an organocatalyst selected according to one or more embodiments of the present invention allows for the formation of coatings using a variety of activated fluoroarenes and silyated thiol nucleophiles according to the reaction schemes depicted in FIGS. 3 and 4. These results demonstrate the efficacy of this newly developed polymer forming reaction for accessing new fluorinated materials and their use in hydrophobic coatings. Given the general effectiveness of these conditions for a wide variety of activated fluoroarenes and silyated thiol nucleophiles (see FIG. 4), this can allow for the rapid development of a broad swath of new hydrophobic materials.

General Reagent and Reaction Information

All reactions were performed on the benchtop with benchtop solvents under an atmosphere of air unless otherwise noted. All thioether monomers were stored in a nitrogen-filled glove box. Small amounts (~500 mg) were removed and stored in a vacuum desiccator with calcium sulfate as the desiccant for benchtop experiments. DMF for glovebox experiments was passed through two packed alumina columns under nitrogen and then stored in the glovebox over freshly activated 3 Å molecular sieves. All other reagents and solvents were commercially available and were used as received.

General Analytical Information

The $^1$H NMRs of the polymers were recorded using a Bruker Avance 400 spectrometer, operated at 400 MHz with the solvent proton signal as the internal reference. SEC was conducted using THF (1.0 mL/min) as the eluent for monitoring the polymer conversion. THF-SEC was recorded on a Waters 2695D (Waters Corporation, USA) Separation Module equipped with an Optilab rEX differential refractometer (Wyatt Technology Corporation, U.S.A.) and Waters HR-4E as well as HR-1 columns (Waters Corporation, USA). Polymer solutions were prepared at a known concentration (ca. 3 mg/mL) and an injection volume of 100 µL was used. Data collection and analysis were performed using the Astra software (Wyatt Technology Corporation, USA; version 5.3.4.20). The columns were calibrated with series of polystyrene standards ranging from Mp=360 Da to Mp=778 kDa (Polymer Standard Service, USA). Thermogravimetric analyses (TGA) were performed on a TA Instruments Q500. The samples (7 to 9 mg of polymer isolated by precipitation) were scanned from RT to 500 degrees Celsius at a 5 degrees Celsius/min heating rate under an $N_2$ atmosphere. Differential scanning calorimetry (DSC) analyses were performed on a TA Instruments Q2000. The samples (7 to 9 mg of polymer isolated by precipitation) were scanned at a 5 degrees Celsius/min heating rate in aluminum closed pans. The samples were subjected to a −80° C. to 300 degrees Celsius scan. Dynamic Mechanical Analyses (DMA) were performed on a TA Instruments DMA 2980 using a dual cantilever. The samples (approx. 12*6*1 mm) were prepared by coating braids with NMP solutions of 1a and hexafluorobenzene, which were quickly mixed before deposition and curing at 220 degrees Celsius for 1 h to eliminate the NMP solvent and reaction by-products. The braids were solicited from −80° C. to 300 degrees Celsius at a 5 degrees Celsius/min heating rate twice and the reported trace corresponds to the second scan (first and second scans showed similar results max. +/−8 degrees Celsius for the tan δ maxima).

Synthesis of Monomers 2,2,11,11-tetramethyl-3,10-dithia-2,11-disiladodecane (1a): A 500 mL round bottom flask under an atmosphere of nitrogen equipped with a magnetic stir-bar was charged with 1,6-hexanedithiol (2.5 mL, 22.3 mmol), triethylamine (6.2 mL, 49.2 mmol), and hexane (90 mL). TMSCl (6.9 mL, 49.2 mmol) was added via syringe and the reaction mixture was allowed to stir for 18 hours at room temperature. After 18 hours, the solid was removed via filtration and the filtrate was concentrated with the aid of a rotary evaporator. Additional hexane (100 mL) was added to the residue and the mixture was filtered again to remove any residual solid. The filtrate was concentrated with the aid of the rotary evaporator to provide the desired product as a colorless oil (4.54 g, 69%). $^1$H NMR (400 MHz, CDCl$_3$) δ 2.41 (m, 4H), 1.52 (m, 4H), 1.32 (m, 4H), 0.22 (s, 18H). $^{13}$C NMR (100 MHz, CDCl$_3$) δ 32.8, 28.2, 26.2, 0.9.

bis(4-(((trimethylsilyl)thio)phenyl)sulfane (referred to herein as 2a): A 500 mL round bottom flask under an atmosphere of nitrogen equipped with a magnetic stir-bar was charged was charged with 4,4'-thiodibenzenethiol (5.0 g, 20 mmol), Et$_2$O (100 mL), and CH$_2$Cl$_2$ (40 mL). TMSCl (5.6 mL, 44 mmol) was added followed by Et$_3$N (6.1 mL, 44 mmol). After stirring at room temperature for 18 hours, the solid was removed by filtration and the filtrate was concentrated with the aid of a rotary evaporator. The residue was redissolved in Et$_2$O (150 mL), filtered, and concentrated to give the desired product as an off-white solid (6.6 g, 84%). Note: The compound was used without further purification due to the sensitivity of the compound to moisture. As a result, the $^{13}$C NMR was observed to contain residual impurities, likely due to small amounts of decomposition of the title compound. $^1$H NMR (400 MHz, CDCl$_3$) δ 7.44-7.42 (m, 4H), 7.30-7.28 (m, 4H), 0.37 (s, 18H). $^{13}$C NMR (100 MHz, CDCl$_3$) δ 135.8, 134.3, 132.5, 131.2, 130.8, 130.4, 130.2, 1.0.

Procedure for Polymerization of Silyl Protected Dithiols and Perfluoroarenes

An 8 mL screw-cap vial equipped with a magnetic stir-bar was charged with the thioether monomer 1a or 2a (1 equiv) and fluoroarene (1-1.05 equiv), if solid. Solvent was then added, followed by any monomer that is a liquid (thioether or fluoroarene). The reaction mixture was then stirred on a stir plate to fully mix and dissolve the monomers. The catalyst (0.5-10 mol %) was then added and the reaction mixture was stirred for the indicated time at the specified temperature. Following completion of the reaction, methanol was added (8 mL) to precipitate the polymer. The solid was collected via centrifugation and decanting of the supernatant. Additional methanol (8 mL) was added and the process was repeated a second time. After drying, the sample was analyzed via NMR and SEC.

Polymer 1b: In a nitrogen filled glovebox and in accordance with the general procedure, a mixture of 1a (84 µL, 0.25 mmol), hexafluorobenzene (28 µL, 0.25 mmol), DBU (20 µL of a 0.062 M stock solution in DMF), and DMF (0.25 mL) were stirred at room temperature for 15 minutes. After 15 minutes, the vial was removed from the glovebox and subjected to the workup in accordance with the general procedure, the polymer was isolated as a white solid. $M_n$=33210 g/mol, $M_w$=120743 g/mol, Đ=3.64. $^1$H NMR (400 MHz, CDCl$_3$) δ 2.92 (m, 4H), 1.56 (m, 4H), 1.41 (m, 4H). $^{19}$F NMR (128 MHz, CDCl$_3$) −135.07. T$_g$ (DSC): −18 degrees Celsius.

Polymer 2b: In accordance with the general procedure, a mixture of 1a (161 μL, 0.48 mmol), decafluorobiphenyl (167 mg, 0.5 mmol), DBU (0.75 μL, 0.005 mmol; added as a stock solution in 0.1 mL DMF), and DMF (0.5 mL) were stirred at room temperature for 15 minutes. Following the workup in accordance with the general procedure, the polymer was isolated as a white solid. M$_n$=15701 g/mol, M$_w$=40353 g/mol, Đ=2.57. $^1$H NMR (400 MHz, CDCl$_3$) δ 3.03 (m, 4H), 1.65 (m, 4H), 1.48 (m, 4H). $^{19}$F NMR (128 MHz, CDCl$_3$) δ −134.6 (m, 4F), −139.2 (m, 4F). T$_g$ (DSC): 16.7 degrees Celsius.

Polymer 2c: In a nitrogen filled glovebox and in accordance with the general procedure, a mixture of 2a (197 mg, 0.50 mmol), decafluorobiphenyl (168 mL, 0.50 mmol), and DMF (0.5 mmol) were stirred at room temperature for 5 minutes. Following the workup in accordance with the general procedure, the polymer was isolated as a white solid. Note: Polymer retained residual DMF after workup. M$_n$=7768 g/mol, M$_w$=47026 g/mol, Đ=6.05. $^1$H NMR (400 MHz, CDCl$_3$) δ 7.34 (m, 8H). $^{19}$F NMR (128 MHz, CDCl$_3$) δ −132.8 (m, 4F), −133.0 (m, 0.5F), −137.9 (m, 4F), −138.1 (m, 0.5F). T$_g$ (DSC): 150 degrees Celsius.

Polymer 2d: In a nitrogen filled glovebox and in accordance with the general procedure, a mixture of 2a (197 mg, 0.50 mmol), hexafluorobenzene (56 μL, 0.50 mmol), DBU (20 μL of a 0.062 M stock solution in DMF), and DMF (0.50 mL) were stirred at room temperature for 10 minutes. Following the workup in accordance with the general procedure, the polymer was isolated as a white solid. T$_g$ (DSC): 48 degrees Celsius. Note: The low solubility of the resulting polymer prevented full analysis by GPC or NMR.

Polymer 2e: In accordance with the general procedure, a mixture of 1a (168 μL, 0.50 mmol), bis(4-fluoro-3-nitrophenyl)sulfone (172 mg, 0.50 mmol), DBU (20 μL of a 0.125 M stock solution in DMF), and DMF (0.5 mL) were stirred at room temperature for 10 minutes. Following the workup in accordance with the general procedure, the polymer was isolated as a light yellow solid. T$_g$ (DSC): 48 degrees Celsius. Note: The low solubility of the resulting polymer prevented full analysis by GPC or NMR.

Procedure for Catalyst Free Control Experiment

In a nitrogen-filled glovebox, an 8 mL screw-cap vial equipped with a magnetic stir-bar was charged with 1a (84 μL, 0.25 mmol), hexafluorobenze (28 μL, 0.25 mmol), and DMF. The reaction mixture was stirred for 40 minutes at room temperature. Following completion of the reaction, methanol was added (8 mL) and no polymer precipitated. PhCF$_3$ (31 μL, 0.25 mmol) was added and an aliquot was removed for $^{19}$F NMR analysis, which indicated no consumption of the hexafluorobenzene.

Procedure for Preparation of Braids for DMA

A screw-cap vial was charged with 1a (229 μL, 0.68 mmol), hexafluorobenzene (80 μL, 0.71 mmol), and NMP (1.5 mL). A separate vial was charged with DBU (10.6 μL, 0.071 mmol) and NMP (0.5 mL). The catalyst and monomer solutions were mixed and the braid was saturated with the mixture. The braid was heated to 60 degrees Celsius for 1 hour then cured at 220 degrees Celsius for 4 hours. A control braid was prepared in the same manner using previously isolated polymer (prepared using the same procedure as 1a) in an NMP solution.

Procedure for the Preparation of Cast Films

An eight (8) ml vial was charged with 1a (229 μL, 0.712 mmol), hexafluorobenzene (80 μL, 0.712 mmol), and NMP (1.5 mL). A second eight (8) ml vial was charged with DBU (11 μL, 0.0712 mmol) and NMP (0.5 mL). The DBU solution was added to the contents of the first vial and briefly mixed before being administered to the surface of a glass slide via pipette. Once the slide had been fully coated, it was placed on a hot plate and cured at 60 degrees Celsius for 1 hour and then 220 degrees Celsius for 4 hours. After the curing was complete, the contact angle of the film was then measured.

Procedure for the Preparation of Spin-Coated Films

A sample of polymer prepared according to one or more embodiments of the present invention was dissolved in THF (100 mg/mL). The solution was placed on a silicon wafer and spin-coated at 4000 rpm for 30 seconds. After completion, the contact angle of the film was analyzed.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments described herein.

What is claimed is:

1. A method for forming an organocatalyzed polythioether coating, the method comprising:
    providing a first solution comprising a bis-silylated dithiol and a fluoroarene, the bis-silylated dithiol comprising 2,2,11,11-tetramethyl-3,10-dithia-2,11-disiladodecane;
    providing a second solution comprising an organocatalyst;
    mixing the first solution and the second solution to form a mixed solution;
    applying the mixed solution to a substrate; and
    curing the substrate.

2. The method of claim 1, wherein curing the substrate further comprises curing the substrate at a temperature of about 220 degrees Celsius for about six hours.

3. The method of claim 1, wherein the fluoroarene comprises hexafluorobenzene.

4. The method of claim 1, wherein the first solution further comprises N-methyl-2-pyrrolidone (NMP).

5. The method of claim 1, wherein the organocatalyst comprises 1,8-diazabicyclo[5.4.0]undec-7-ene (DBU).

6. The method of claim 1, wherein the organocatalyst comprises 1,5,7-triazabicyclo[4.4.0]dec-5-ene (TBD).

7. The method of claim 1, wherein the second solution further comprises N-methyl-2-pyrrolidone (NMP).

8. A method for forming an organocatalyzed polythioether coating on an implantable medical device, the method comprising:
    providing a first solution comprising a bis-silylated dithiol and a fluoroarene, the bis-silylated dithiol comprising a thioether of 4,4'-thiodibenzenethiol;
    providing a second solution comprising an organocatalyst;
    mixing the first solution and the second solution to form a mixed solution;
    applying the mixed solution to a surface of the implantable medical device; and
    curing the mixed solution to form the organocatalyzed polythioether coating.

9. The method of claim 8, wherein curing the mixed solution further comprises curing the mixed solution at a temperature of about 220 degrees Celsius for about six hours.

10. The method of claim 8, wherein the organocatalyzed polythioether coating comprises the substructure:

wherein n is greater than 1, R is a silyated thiol nucleophile, and Ar is an activated fluoroarene.

11. The method of claim 8, wherein the organocatalyzed polythioether coating comprises the substructure:

(I)

or (II)

wherein n is greater than 1.

12. The method of claim 8, wherein the fluoroarene comprises hexafluorobenzene.

13. The method of claim 8, wherein the first solution further comprises N-methyl-2-pyrrolidone (NMP).

14. The method of claim 8, wherein the organocatalyst comprises 1,8-diazabicyclo[5.4.0]undec-7-ene (DBU).

15. The method of claim 8, wherein the organocatalyst comprises 1,5,7-triazabicyclo[4.4.0]dec-5-ene (TBD).

16. The method of claim 8, wherein the second solution further comprises N-methyl-2-pyrrolidone (NMP).

* * * * *